United States Patent [19]

Froelich et al.

[11] Patent Number: 4,874,122
[45] Date of Patent: Oct. 17, 1989

[54] BENT BACK BOX STAPLE AND STAPLE CLOSING MECHANISM WITH SPLIT ACTUATOR

[75] Inventors: Harold E. Froelich, Minn.; Floyd L. Foslien, both of St. Paul, Minn.

[73] Assignee: Minnesota Mining and Manufacturing Company, St. Paul, Minn.

[21] Appl. No.: 238,972

[22] Filed: Aug. 25, 1988

Related U.S. Application Data

[63] Continuation of Ser. No. 885,221, Jul. 14, 1986, abandoned.

[51] Int. Cl.$^4$ .................. B25C 5/06; A61B 17/04
[52] U.S. Cl. .................... 227/19; 411/457; 128/334 R
[58] Field of Search ............ 227/19, 83, DIG. 15, 227/DIG. 15 C; 411/457, 471, 472, 473; 128/337, 334 R, 335

[56] References Cited

U.S. PATENT DOCUMENTS

| | | | |
|---|---|---|---|
| 3,643,851 | 2/1972 | Green et al. | 227/19 |
| 3,815,476 | 6/1974 | Green et al. | 91/410 |
| 3,837,555 | 9/1974 | Green | 227/130 |
| 3,873,016 | 3/1975 | Fishbein | 227/83 |
| 4,026,520 | 5/1977 | Rothfuss et al. | 254/28 |
| 4,043,504 | 8/1977 | Hueil et al. | 227/116 |
| 4,127,227 | 11/1978 | Green | 227/83 |
| 4,202,480 | 5/1980 | Annett | 227/8 |
| 4,256,513 | 3/1981 | Moshofsky | 227/120 |
| 4,321,002 | 3/1982 | Froehlich | 411/457 |
| 4,331,277 | 5/1982 | Green | 227/19 |
| 4,375,866 | 3/1983 | Giersch et al. | 227/85 |
| 4,403,693 | 9/1983 | Froehlich | 206/339 |
| 4,470,532 | 9/1984 | Froehlich | 227/19 |
| 4,477,007 | 10/1984 | Foslien | 227/19 |
| 4,477,008 | 10/1984 | Struble | 227/19 |
| 4,519,532 | 5/1985 | Foslien | 227/8 |

FOREIGN PATENT DOCUMENTS

| | | |
|---|---|---|
| 0061867 | 10/1982 | European Pat. Off. |
| 0085930 | 8/1983 | European Pat. Off. |
| 0094752 | 11/1983 | European Pat. Off. |
| 0229453 | 7/1987 | European Pat. Off. |

*Primary Examiner*—Frank T. Yost
*Assistant Examiner*—James L. Wolfe
*Attorney, Agent, or Firm*—Donald M. Sell; Walter N. Kirn; Stephen W. Bauer

[57] ABSTRACT

An unused open wire skin staple having a generally U-shaped central portion and outer portions terminating in sharp points that can be closed to a rectangular shape by straightening the central portion. The staple can be closed between an anvil having spaced support surfaces for spaced points along the outer curved surface of the central portion, and a ram with separable end parts that can apply both longitudinal and transverse forces to close the staple around the anvil.

8 Claims, 3 Drawing Sheets

BENT BACK BOX STAPLE AND STAPLE CLOSING MECHANISM WITH SPLIT ACTUATOR

This is a continuation of application Ser. No. 885,221 filed July 14, 1986, now abandoned.

TECHNICAL FIELD

The present invention relates to shapes for unused open wire staples for suturing living tissue, and to the shapes of rams and anvils used to close such staples.

BACKGROUND ART

The art is replete with shapes of unused open wire staples for suturing living tissues, and rams and anvils of various shapes used to close such staples. U.S. Pat. Nos. 3,873,016; 4,202,480; 4,256,251; 4,321,002; 4,477,007; 4,477,008; and 4,519,532 provide illustrative examples.

Such prior art unused open wire staples have included a staple having a straight central portion with straight pointed end portions projecting at right angles thereto (such as is illustrated in FIG. 4 of U.S. Pat. No. 4,202,480 incorporated herein by reference), which staple may be bent at two spaced locations along its central portion to form a generally rectangular closed staple (see FIG. 6 of U.S. Pat. No. 4,202,480) and is called a "box" staple herein. The side of the closed box staple opposite its end portions can subsequently be bent into a U-shape to retract the staple from the skin and underlying tissue as is illustrated in U.S. Pat. No. 4,026,520 (incorporated herein by reference). Such box staples have been widely used and have been well accepted by the medical community. This is at least partially so because of the currently preferred method for stapling skin. It is known that the inner surfaces of skin edge portions separated by an injury or an incision must make contact for proper healing to occur, and that if skin edge portions are inverted during stapling (i.e., positioned with their outer surfaces face to face) poor healing with the probability of scarring will result. Thus skin edge portions to be stapled together typically are everted (i.e., tented upwardly) with the inner surface of the skin edge portions pressed together, and the staple is applied over the everted skin edge portions to hold them together. When the box staple is so used, the parts of the skin edge portions pierced by the staple initially are positioned along its aligned end portions on the side of the closed box staple adjacent the skin portions being stapled. With time, tensions in the skin transverse to the opening being stapled closed will cause the parts of the skin portion pierced by the staple to move from around the adjacent end portions (which then become buried in tissue beneath the joined skin portions) to positions around the opposite side portions of the closed staple at which the skin edge portions lose some of their original eversion and are more in alignment. With the box staple, however, this movement of the skin does not occur immediately due to the restriction caused by the right angle corners between the end portions and side portions of the staple around which corners those parts of the skin portions must pass. Thus, the skin portions have a tendency to remain everted along the entire length of the opening being closed at least for the period of time required to complete stapling together of the skin edge portions, and a person who has completed the stapling can visually assure himself after the stapling of the skin edge portions is complete that the skin edge portions are still in a position which will afford proper healing. The box type staple, however, suffers from the disadvantage of requiring the staple to be bent sharply in two locations to close it in a manner which has required the use of metal rams and anvils and the application of substantial closing force; and causes some damage to the skin, particularly when the parts of the skin edge portions pierced by the staple move around the right angle bends in the staple as described above.

Another prior art staple for suturing living tissue described in U.S. Pat. No 4,321,002 comprises a generally U-shaped central portion having at least one arcuate part and curved outer portions terminating in sharp points. That staple can be closed by bending generally straight the arcuate part or parts so that the curved outer portions will smoothly enter and gather living tissue such as skin portions. During such closure the sharp points on the outer portions move to adjacent generally aligned positions to provide a generally D-shaped staple. As with the previously described box staple, the central portion of the closed D-shaped staple can subsequently be bent to retract the outer portions of the staple from the tissue.

The force needed to close such a D-shaped staple having only one arcuate part is substantially reduced for a similarly sized staple from the force required to close the box staple described above, so that the D-shaped staple can be closed with a ram and anvil made of polymeric material such as is described in U.S. Pat. Nos. 4,477,008 and 4,519,532 (incorporated herein by reference). Also the curved outer portions can cause a reduced amount of damage to skin and tissue during use compared to the box staple. Such D-shaped staples, however, have not been received by the medical community with the enthusiasm one might expect presumably in part because the closed D-shaped staple will not hold joined skin portions in an everted position as long as a closed box staple. The stapled skin portions easily and quickly move along the arcuate portions of the D-shaped staple to a generally aligned position (which aligned position provides as good or better healing than the everted position) typically before the person stapling together the skin edge portions has completed the required stapling, so that that person can not observe all of the stapled skin edge portions in an everted position and thus be sure that some of the skin portions will not subsequently become inverted.

Also, even though the closing force of the "D" shaped staple having only one arcuate part is sufficiently low that rams and anvils used to close it can be made of polymeric material, significant wear can occur on such polymeric rams and anvils when they are used to close a large number of staples; and it has been found that staples can slip sideways along the surfaces of the polymeric rams and anvils contacting the staple (a phenomenon not observed between metal anvils, rams and staples) which can result in improperly shaped closed staples.

Another general problem that has existed in the design of rams and anvils for staplers has been to deal with the tendency for the central portion of the open staple to bend away from the anvil toward the ram as a result of forces by which the staple is bent to its closed position. One suggested approach for use with box staples has been to arch the center portion of the open staple toward the anvil so that it bends to a generally straight position as the staple is bent closed as is illustrated in U.S. Pat. No. 4,256,251 (see FIGS. 12 and 19). Another approach being used is to shape the central portion of the ram so that it will straighten the bowed central portion of the staple by bending it against the anvil after the staple is essentially closed as is done in the "Precise" TM stapler sold for several years by Minnesota Mining and Manufacturing Company, St. Paul, Minn. Yet another approach has been to provide a support to prevent such bending on the side of the central portion of the staple opposite the ram as is described in U.S. Pat. No. 4,127,227.

However prevented, it is preferable that the central portion of the staple is not bowed significantly upwardly after the staple is closed, since if such a bow is present, pressure from the jaws of a staple remover of the type described in U.S. Pat. No. 4,026,520 will cause crank-like forces tending to rotate the staple around its central portion as it is bent open, which rotation of the staple can cause the staple to be bent out of its plane which may damage the tissue from which the staple is being removed.

DISCLOSURE OF THE INVENTION

The present invention provides a novel unused open wire staple for suturing living tissue that can be bent closed using a ram and anvil of polymeric material to form a rectangular or box shaped closed staple, and a novel shape for a ram and anvil which can be made of polymeric materials by which the new staple or the D-shaped staple described above can be bent closed without slipping sideways on the anvil and with substantially less initial closing force than is needed with prior art ram and anvil combinations, and which applies forces in a manner that reduces the tendency for the central portion of the staple to bend away from the anvil as it is closed.

According to the present invention there is provided an unused open wire staple for suturing living tissue, which open staple comprises a generally U-shaped central portion having at least one arcuate part, and outer portions terminating in sharp points. The outer portions each comprise a generally straight proximal part (generally straight as used herein may include a slight curve in the part) and a generally straight distal part disposed at about a right angle to each other with the sharp point being on the end of the distal part opposite the proximal part. The end of the proximal part opposite the distal part is disposed at about a right angle to and is connected to one end of the central portion. The staple is closable by bending generally straight the arcuate part or parts of the central portion so that the outer portions can enter and gather living tissue. During such closure the sharp points on the distal parts move to adjacent positions with the distal parts generally aligned with each other to provide a generally rectangular or box shaped closed staple. The central portion of the closed staple can subsequently be bent to retract the outer portions of the staple from the living tissue in the manner illustrated in U.S. Pat. No. 4,026,520.

Preferably for ease of closing the staple the U-shaped portion of the staple has only one arcuate part, however, two spaced arcuate parts may also be used which can provide more gather than a single arcuate part.

Also, according to the present invention there is provided a stapler adapted for closing an open wire staple of the type used to suture living tissue, which type of staple comprises a generally U-shaped central portion having at least one arcuate part and outer portions terminating in sharp points, with the end parts of each outer portion opposite the sharp point being disposed at about a right angle to and being connected at a first corner to one end of the central portion (e.g., the novel staple described above or the open staple described in U.S. Pat. Nos. 4,321,002; 4,477,008 and 4,159,532); which staple is closable by bending generally straight the arcuate part of its central portion so that its outer portions can enter and gather living tissue, during which closure the sharp points on the distal parts move to adjacent positions with the distal parts generally aligned with each other to provide a closed staple (generally aligned as used herein includes a slight overlapping of the distal parts).

The stapler includes an anvil which may be of polymeric material and has spaced support surfaces and a recess between the support surfaces adapted to receive a central part of the generally U-shaped central portion of the staple; and a ram (which also may be of polymeric material) comprising an end portion of resiliently flexible material having two separated parts each having an end surface adapted to engage the open staple, which end surfaces have spaced outer portions and inner portions recessed from the outer portions and extending generally transverse of the ram. The end surfaces are radiused from their outer portions to their inner portions to form opposed radiused surface portions adapted to engage along the outer portions of the open staple. The junctures between the radiused surface portions and the inner surface portions form sockets adapted to engage the first corners of the staple when the central portion of the staple is partially straightened; and the inner surface portions are disposed to straighten the central portion across the anvil to complete closure of the staple.

Means are provided on the staple for moving the ram toward the anvil to close the staple around the anvil with parts of the central portion of the staple between the first corners of the staple and the outer surface of the central portion supported against the spaced support surfaces by sequentially (1) pressing the radiused end surface portions of the ram against the outer portions of the staple to resiliently spread the parts of the ram and apply forces both longitudinally and transversely of the ram to generally straighten the central portion of the staple around pivot points provided by the spaced support surfaces; (2) to subsequently press the surfaces forming the sockets on the ram against the first corners of the staple to partially straighten the central portion of the staple across the support surfaces; and (3) to then engage the inner surface portions of the anvil with the central portion of the staple to straighten it across the support surfaces and complete closure of the staple.

The application of forces both longitudinally and transversely of the ram provides a resultant force which both closes the staple with less initial force applied to the ram than with a ram that does not have resiliently spreadable parts and in combination with the two point support of the anvil can straighten the central portion of a staple having one arcuate part with almost no tendency for the central part of it to bend away from the anvil toward the ram. Preferably the resiliency of the parts and the location of the radiused end portions as they move along the staple are selected so that the forces tending to straighten the U-shaped central portion of the staple are applied along lines generally parallel to the axes of the generally straight end parts of the U-shaped central portion and spaced from the axis of those end parts on the sides of those end parts opposite the center of the U-shaped portion a distance about equal the distance that would theoretically make such a force cause a long column to buckle, so that the forces instead tend to straighten the central part of the central portion. Tests have shown that straightening forces estimated using the column bending theoretical formulas in this way are very close to actual measured forces needed to straighten the central part in a staple.

Also, the application of forces both longitudinally and transversely by the separable parts of the ram and the spaced support surfaces on the anvil keep the staple essentially centered across the anvil and the ram so that a properly shaped closed staple results.

BRIEF DESCRIPTION OF THE DRAWING

The present invention will be further described with reference to the accompanying drawing wherein like reference numerals refer to like parts in the several views, and wherein.

DETAILED DESCRIPTION

Figure 1:
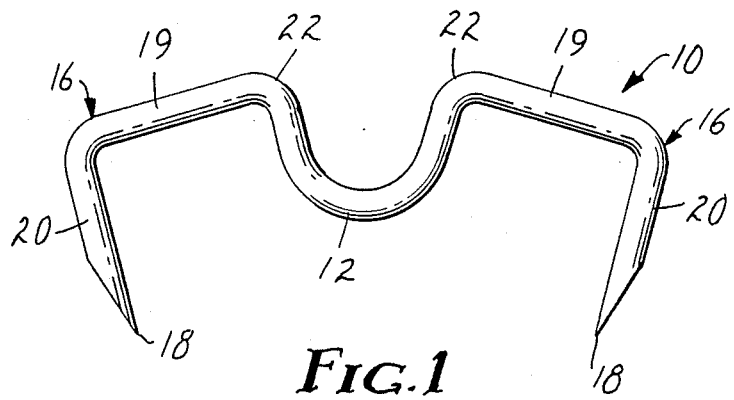
FIG. 1 is a plan view of an open wire staple for suturing living tissue according to the present invention.

Referring now to FIG. 1 of the drawing there is illustrated an unused open wire staple for suturing living tissue according to the present invention, generally designated by the reference numeral 10.

Figure 2:
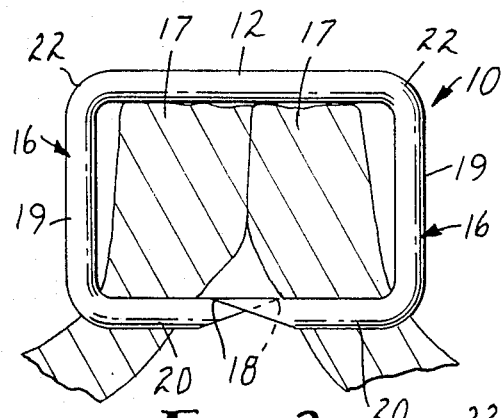
FIGS. 2 and 3 are plan views of the staple of FIG. 1 closed in living tissue.

As is best seen in FIG. 1, the open wire staple 10 comprises a generally U-shaped central portion 12 having one arcuate part; and outer portions 16 terminating in sharp points 18. The outer portions 16 each comprise a generally straight proximal part 19 and a generally straight distal part 20 with the parts 19 and 20 disposed at about a right angle to each other and with the sharp point 18 being on the end of each distal part 20 opposite the proximal part 19. The end of the proximal part 19 opposite the distal part 20 is disposed at about a right angle to and is connected at a first corner 22 to one end of the central portion 12. The staple is closable to the closed position shown in FIGS. 2 and 3 by bending generally straight the arcuate part of its central portion 12 so that the outer portions 16 can enter and gather living tissue such as adjacent skin edge portions 17. During such closure, the sharp points 18 on the distal parts 20 move to adjacent positions with the distal parts 20 generally aligned with each other to provide a generally rectangular or box shaped closed staple. Typically, the skin edge portions 17 are initially everted as shown in FIG. 2 so that only the distal parts 20 pierce the skin edge portions 17. Subsequently, as described above in the Background Art portion of this application, tension in the skin edge portions 17 causes them to move around the right angle corners between the distal parts 20 and proximal parts 19 to the generally aligned positions shown in FIG. 3.

Figure 4:
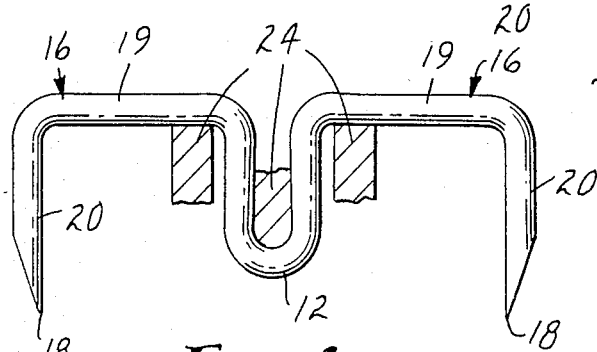
FIG. 4 is a plan view of the staple of FIG. 2 bent to an open position by a staple remover.

As shown in FIG. 4, the central portion 12 of the closed staple can subsequently be bent to a U-shape b the jaws 24 of the type of staple remover described in U.S. Pat. No. 4,026,520 to retract the outer portions 16 of the staple 10 from the skin portions 17.

The staple is preferably formed of a wire with a circular cross section (e.g., 0.0225 inch diameter) and as can be seen in FIG. 1, the central part of the central portion 12 of the unused open staple 10 is bent in a semicircular arc (e.g., 0.0666 inch radius to its outer surface). The outer parts of the central portion 12 diverge from parallel by about 30 degrees so that the proximal parts 19 of the staple 10 correspondingly are disposed to form an angle of about 150 degrees with each other. Alternatively the outer parts of the central portion 12 could be disposed between positions parallel with each other so that the proximal parts 19 are aligned, and portions diverging from parallel by about 60 degrees so that the proximal parts 19 form an angle of about 120 degrees with each other.

Referring now to FIGS. 5 through 8, there is schematically illustrated a stapler 30 for closing the staple 10, which stapler 30 may be in the form of the stapler illustrated in U.S. Pat. No. 4,519,532 incorporated herein by reference.

Generally, as illustrated, the stapler 30 comprises an anvil 32 having spaced support surfaces 34 and a recess 36 between the support surfaces 34 adapted to receive a central part of the generally U-shaped central portion 12 of the staple 10. Also, the stapler 30 comprises a ram 40 comprising an end portion of resiliently flexible material having two spaced and separated parts 42 each having a concave end surface adapted to engage the open staple 10. The end surfaces have spaced outer portions 46 and inner portions 48 recessed from the outer portions and extending generally transverse of the ram 40. The end surfaces are radiused from their outer portions 46 to their inner portions 48 to form opposed radiused surface portions 50 adapted to engage along the outer portions 16 of the open staple. The junctures between the radiused surface portions 50 and the inner surface portions 48 form sockets adapted to engage the first corners 22 of the staple 10 when the central portion 12 is partially straightened and the inner surface portions 48 are disposed to straighten the central portion 12 across the anvil 32 when the staple 10 to complete closure of the staple 10.

Also included in the stapler are means 52 for moving the ram 40 toward the anvil 32 to close the staple 10 around the anvil 32 with the central portion 12 of the staple 10 supported against the spaced support surfaces 34, which means 52 may be in the form of the manually operable toggle joint linkage type drive described in U.S. Pat. No. 4,519,532. Such movement of the ram 40 by such means 52 will sequentially (1) press the radiused end surface portions 50 of the ram 40 against the proximal parts 19 of the outer portions 16 of the staple 10 (FIG. 5) to resiliently spread the parts 42 of the ram 40 and apply forces both longitudinally and transversely of the ram 40 to generally straighten the central portion 12 of the staple 10 (FIG. 6); (2) to subsequently press the surfaces 50 and 48 forming the sockets against the first corners 22 of the staple 10 to generally straighten the central portion 12 (FIG. 7); and (3) to then engage the inner surface portions 48 of the ram 40 with the central portion 12 of the staple to straighten the central portion 12 across the anvil 32 and complete closure of the staple 10.

Figure 3:
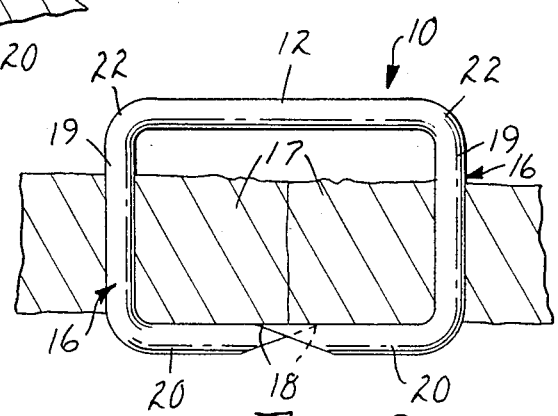
Figure 8:
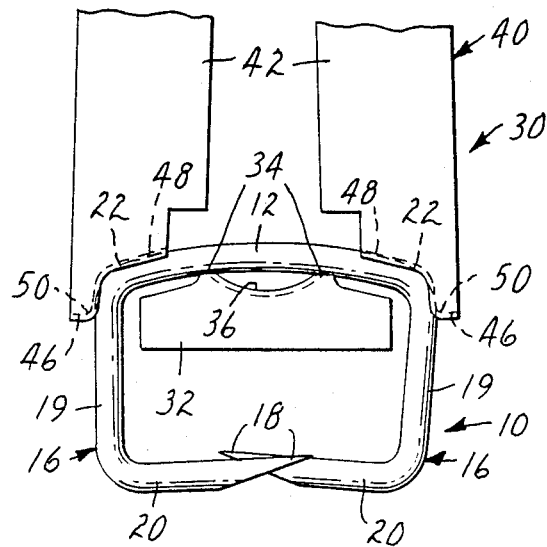

The inner surface portions 48 of the ram are each disposed at a slight angle with respect to a line at a right angle to the longitudinal centerline of the ram 40 (e.g., 15 degrees) and are relieved opposite the support surfaces 34 which causes them to bend the central portion 12 of the staple into a slight arch around the support surfaces 34 of the anvil 32 (FIG. 8). The elasticity in the staple wire will cause this arch to straighten when the pressure between the ram 40 and anvil 32 is removed, however, to provide a straight central portion 12 for the closed staple 10 as is shown in FIGS. 2 and 3.

Figure 5:
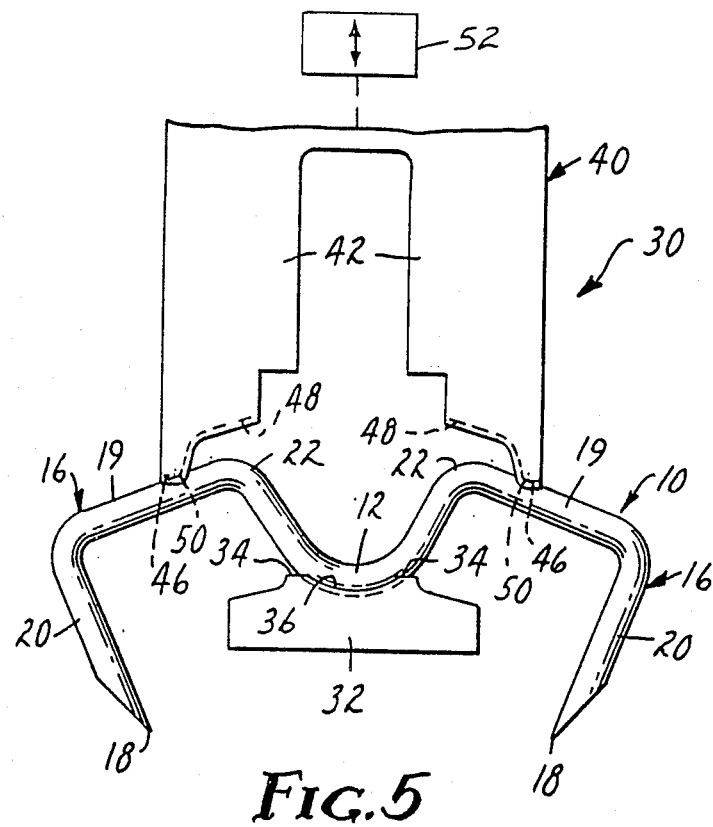
FIGS. 5 through 8 are fragmentary schematic views sequentially illustrating closing of the open wire staple of FIG. 1 using a ram and anvil structure according to the present invention.
Figure 6:
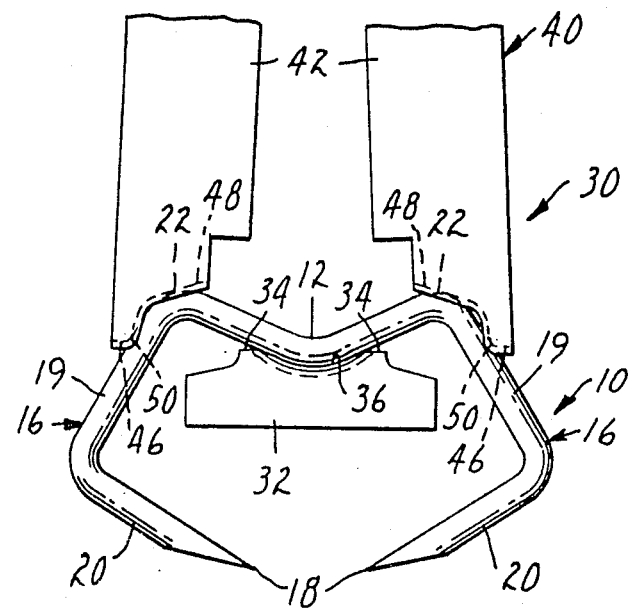
Figure 7:
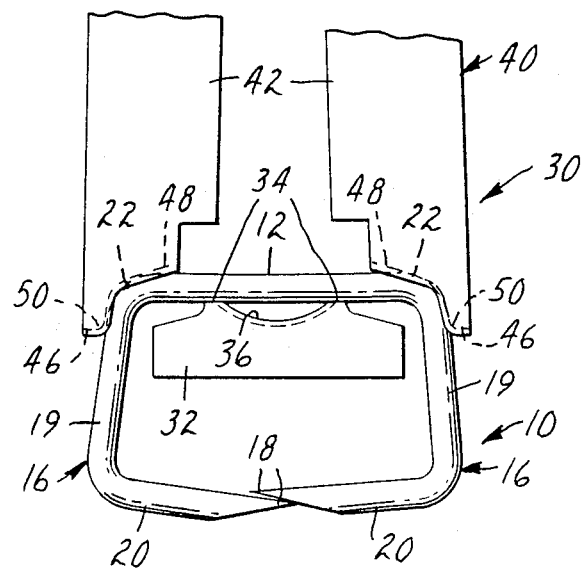

Preferably the resiliency and geometry of the ram 40 are selected so that spreading of the parts 42 of the ram 40 during movement of the ram 40 between the positions shown in FIGS. 5 and 6 causes a resultant force to be applied to the proximal parts 19 of the staple 10 which is generally parallel to the axes of the generally straight end parts of the U-shaped central portion 12 and is spaced from the axis of those end parts on the sides of those end parts opposite the center of the U-shaped portion 12 a distance about equal the distance that would theoretically make such a force cause a long column the diameter of the staple 10 to buckle, so that the forces instead tend to straighten the central part of the central portion 12. While it is almost impossible to maintain precise force alignment of this type, it has been found that the closer such alignment can be maintained the less force is required to initially bend the staple 10 toward a closed position, which is particularly advantageous for a ram 40 driven by a toggle joint linkage type drive with which it is more difficult to develop force at the ram 40 during initial movement of the ram 40 than later in the movement of the ram 40.

The present invention has now been described with reference to one embodiment thereof. It will be apparent to those skilled in the art that many changes can be made in the embodiment described without departing from the scope of the present invention. For example, the generally U-shaped central portion of the staple 10 can alternately be shaped like the central portion 60 of the staple 13 described in U.S. Pat. No. 4,321,002 to have two spaced arcuate parts 61. This provides a staple that can provide more gather to pull together skin portions it engages, however, the staple cannot be closed by the type of ram 40 and anvil 32 illustrated above without some bending of the center of its central portions away from the anvil 32 toward the ram 40. Thus the scope of the present invention should not be limited to the structures described in this application, but only by structures described by the language of the claims and the equivalents of those structures.

We claim:

1. An unused open wire staple for suturing living tissue, said open staple comprising a generally U-shaped central portion having opposite ends and at least one arcuate part; and outer portions terminating in sharp points, said outer portions each comprising a generally straight proximal part and a generally straight distal part with said parts disposed at about a right angle to each other and with said sharp point being on the end of said distal part opposite said proximal part, and the end of said proximal part opposite said distal part being disposed at about a right angle to and connected to one end of said central portion, said staple being closable by bending generally straight the arcuate part of said central portion adjacent each of said outer portions so that said outer portions can enter and gather living tissue, during such closure the sharp points on said distal parts moving to adjacent positions with said distal parts generally aligned with each other to provide a generally rectangular closed staple, and the central portion of the closed staple subsequently being bendable to retract the outer portions of the staple from the living tissue, the distal parts having a length sufficiently greater than the length of the central portion that the sharp points of the outer portions overlap when the staple is closed.

2. An unused open wire staple for suturing living tissue according to claim 1 wherein the U-shaped portion of said staple has only one arcuate part.

3. An unused open wire staple for suturing living tissue according to claim 1 wherein the U-shaped portion of said staple has two spaced arcuate parts.

4. A staple according to claim 1 wherein the proximal parts of the unused staple define lines disposed at an angle of approximately 120–150 degrees with respect to one another, and the distal parts of the unused staple converge toward one another toward the sharp points at an angle of approximately 30–60 degrees.

5. A staple according to claim 4 wherein the arcuate part forms a semicircular arc having a radius of curvature of approximately 1.8 mm.

6. A stapler comprising:

an open wire staple for suturing living tissue, said open staple comprising a generally U-shaped central portion having opposite ends and at least one arcuate part; and outer portions terminating in sharp points, the parts of each outer portion opposite said sharp point being disposed at about a right angle to and being connected at a first corner to one end of said central portion, said staple being closable by bending generally straight the arcuate part of said central portion adjacent each of said outer portions so that said outer portions can enter and gather living tissue, during which closure the sharp points on said outer portions move to adjacent positions generally aligned with each other to provide a closed staple;

an anvil having spaced support surfaces and a recess between said support surfaces adapted to receive a central part of the generally U-shaped central portion of said staple;

a ram comprising a unitary end portion of resiliently flexible material having two separated parts each having an end surface adapted to engage said open staple, said end surfaces having spaced outer portions and inner portions recessed from said outer portions and extending generally transverse of said ram, said end surfaces being radiused from said outer portions to said inner portions to form opposed radiused surface portions adapted to engage along the outer portions of said open staple, the junctures between said radiused surface portions and said inner surface portions forming sockets adapted to engage said first corners of said staple when said central portion is partially straightened and said inner surface portions being disposed to straighten said central portion across said anvil to complete closure of said staple; and means for moving said ram toward said anvil to close said staple around said anvil with the control portion of said staple supported against said spaced support surfaces by sequentially (1) pressing said radiused end surface portions against said outer portions to resiliently spread said parts of said ram and apply forces both longitudinally and transversely of said ram to partially straighten said central portion; (2) to subsequently press the surfaces forming said sockets against the first corners of said staples to substantially straighten said central portion; and (3) to then engage said inner surface portion of said ram with said central portion to sraighten said central portion and complete closure of said staple.

7. A stapler according to claim 6 wherein said generally U-shaped central portion has generally straight end parts, and said radiused end surfaces apply forces against said outer portions generally aligned with said end parts and acting on the sides of said end parts opposite the center of said central portion.

8. A stapler adapted to close an open wire staple for suturing living tissue of the type comprising a generally U-shaped central portion having opposite ends and at least one arcuate part; and outer portions terminating in sharp points, the parts of each outer portion opposite said sharp point being disposed at about a right angle to and being connected at a first corner to one end of said central portion, said staple being closable by bending generally straight the arcuate part of said central portion adjacent each of said outer portions so that said outer portions can enter and gather living tissue, during which closure the sharp points on said outer portions move to adjacent positions generally aligned with each other to provide a closed staple, said stapler comprising:

an anvil having spaced support surfaces and a recess between said support surfaces adapted to receive a central part of the generally U-shaped central portion of the staple;

a ram comprising a unitary end portion of resiliently flexible material having two separated parts each having an end surface adapted to engage the open staple, said end surfaces having spaced outer portions and inner portions recessed from said outer portions and extending generally transverse of said ram, said end surfaces being radiused from said outer portions to said inner portions to form opposed radiused surface portions adapted to engage along the outer portions of the open staple, the junctures between said radiused surface portions and said inner surface portions forming sockets adapted to engage the first corners of the staple when its central portion is partially straightened and said inner surface portions being disposed to straighten the central portion across said anvil to complete closure of the staple; and means for moving said ram toward said anvil to close the staple around said anvil with the central portion of the staple supported against said spaced support surfaces by sequentially (1) pressing said radiused end surface portions against the outer portions of the staple to resiliently spread said parts of said ram and apply forces both longitudinally and transversely of said ram to partially straighten the central portion of the staple; (2) to subsequently press the surfaces forming said sockets against the first corners of the staple to substantially staighten the central portion of the staple; and (3) to then engage said inner surface portions of said ram with the central portion of the staple to straighten the central portion and complete closure of the staple.

* * * * *

UNITED STATES PATENT AND TRADEMARK OFFICE
CERTIFICATE OF CORRECTION

PATENT NO. : 4,874,122

DATED : October 17, 1989

INVENTOR(S) : Harold E. Froehlich, Floyd L. Foslien

It is certified that error appears in the above-identified patent and that said Letters Patent is hereby corrected as shown below:

Front page, No. 75 Inventors: "Froelich" should read --Froehlich--.

Col. 5, line 65, "b" should read --by--.

Col. 8, line 57, "control" should read --central--.

Col. 8, line 68, "tionof" should read --tions of--.

Signed and Sealed this

Thirtieth Day of April, 1991

Attest:

*Attesting Officer*

HARRY F. MANBECK, JR.

*Commissioner of Patents and Trademarks*